US011013507B2

(12) United States Patent
Roberts et al.

(10) Patent No.: US 11,013,507 B2
(45) Date of Patent: May 25, 2021

(54) SUTURE ANCHORS AND METHODS OF USE

(71) Applicant: Oxford Performance Materials, Inc., South Windsor, CT (US)

(72) Inventors: Benjamin Roberts, Manchester, CT (US); Andrus Maandi, Rocky Hill, CT (US); Severine Valdant Zygmont, West Hartford, CT (US); James Porteus, Hartford, CT (US)

(73) Assignee: Oxford Performance Materials, Inc., South Windsor, CT (US)

( * ) Notice: Subject to any disclaimer, the term of this patent is extended or adjusted under 35 U.S.C. 154(b) by 144 days.

(21) Appl. No.: 16/206,099

(22) Filed: Nov. 30, 2018

(65) Prior Publication Data

US 2020/0170633 A1 Jun. 4, 2020

(51) Int. Cl.
*A61B 17/04* (2006.01)
*G16H 20/40* (2018.01)
(Continued)

(52) U.S. Cl.
CPC ........ *A61B 17/0401* (2013.01); *A61F 2/0811* (2013.01); *G16H 20/40* (2018.01); *A61B 2017/00526* (2013.01); *A61B 2017/044* (2013.01); *A61B 2017/0409* (2013.01); *A61B 2017/0412* (2013.01); *A61B 2017/0464* (2013.01); *A61F 2002/0817* (2013.01); *A61F 2002/0852* (2013.01);
(Continued)

(58) Field of Classification Search
CPC .... A61B 2017/0409; A61B 2017/0411; A61B 2017/0445; A61B 2017/0422; A61B 17/0401; A61F 2002/0841
See application file for complete search history.

(56) References Cited

U.S. PATENT DOCUMENTS 3,065,205 A 11/1962 Bonner et al.
3,441,538 A 4/1969 Marks et al.
(Continued)

FOREIGN PATENT DOCUMENTS

WO 2012140427 A1 10/2012
WO 2014100320 A1 6/2014

OTHER PUBLICATIONS

Cheng Z. D. et al: "Polymorphism and crystal structure identification in poly(aryl ether ketone ketone)s," Macromol. Chem. Phys. 197, Abstract pp. 185-213.
(Continued)

*Primary Examiner* — Wade Miles
*Assistant Examiner* — Mohammed S Adam
(74) *Attorney, Agent, or Firm* — Welsh IP Law LLC

(57) ABSTRACT

An anchor system for securing suture tissue to bone. The system includes an anchor and an inserter. The anchor is printed from a polymer by selective laser sintering in accordance with a CAD file having a geometric description of the anchor. A socket at the proximal region of the anchor has cross-section that has a width in a first dimension D1. The system includes an inserter having a protrusion being configured to matingly engage with the socket. The protrusion defines a cross-section that decreases progressively in width in the dimension D1 along the protrusion length distally from the base of the protrusion toward the distal tip of the protrusion.

19 Claims, 10 Drawing Sheets

(51) Int. Cl.
*A61F 2/08* (2006.01)
*A61B 17/00* (2006.01)

(52) U.S. Cl.
CPC .............. *A61F 2220/0016* (2013.01); *A61F 2230/0073* (2013.01); *A61F 2240/002* (2013.01)

(56) References Cited

U.S. PATENT DOCUMENTS

| | | | |
|---|---|---|---|
| 3,442,857 A | 5/1969 | Thornton et al. | |
| 3,516,966 A | 6/1970 | Berr et al. | |
| 4,704,448 A | 11/1987 | Brugel | |
| 4,816,556 A | 3/1989 | Gay et al. | |
| 6,177,518 B1 | 1/2001 | Lahijani | |
| 6,544,281 B2 | 4/2003 | ElAttrache et al. | |
| 6,652,563 B2 | 11/2003 | Dreyfuss | |
| 7,226,469 B2 | 6/2007 | Benavitz et al. | |
| 7,329,272 B2 | 2/2008 | Burkhart et al. | |
| 7,695,495 B2 | 4/2010 | Dreyfuss | |
| 7,883,528 B2 * | 2/2011 | Grafton .............. A61B 17/0401 606/232 |
| 7,993,369 B2 | 8/2011 | Dreyfuss | |
| 8,343,186 B2 | 1/2013 | Dreyfuss et al. | |
| 8,430,909 B2 | 4/2013 | Dreyfuss | |
| 8,623,052 B2 | 1/2014 | Dreyfuss et al. | |
| 8,801,755 B2 | 8/2014 | Dreyfuss et al. | |
| 8,821,541 B2 | 9/2014 | Dreyfuss et al. | |
| 8,968,374 B2 | 3/2015 | Hoof et al. | |
| 9,179,907 B2 | 11/2015 | ElAttrache et al. | |
| 9,277,910 B2 | 3/2016 | Nason et al. | |
| 9,295,460 B2 | 3/2016 | Hoof et al. | |
| 9,402,617 B2 | 8/2016 | Baird | |
| 9,526,493 B2 | 12/2016 | Dreyfuss et al. | |
| 9,549,726 B2 | 1/2017 | Dreyfuss et al. | |
| 9,622,740 B2 | 4/2017 | Nason et al. | |
| 10,000,022 B2 | 6/2018 | DeFelice et al. | |
| 10,143,555 B2 | 12/2018 | DeFelice et al. | |
| 2004/0106950 A1 | 6/2004 | Grafton et al. | |
| 2008/0021474 A1 * | 1/2008 | Bonutti ................ A61F 2/4081 606/64 |
| 2013/0261677 A1 | 10/2013 | Bouduban et al. | |
| 2016/0166245 A1 * | 6/2016 | Patel .................. A61B 17/1615 606/80 |
| 2016/0166284 A1 | 6/2016 | Hacking et al. | |
| 2016/0338689 A1 | 11/2016 | Baird | |
| 2017/0224497 A1 * | 8/2017 | Martin ................ A61F 2/3662 |
| 2018/0200922 A1 | 7/2018 | DeFelice et al. | |

OTHER PUBLICATIONS

Extended European Search Report dated Jan. 9, 2020 Application No. 19206529.0 (related EP case) Applicant: Oxford Performance Materials, Inc.

* cited by examiner

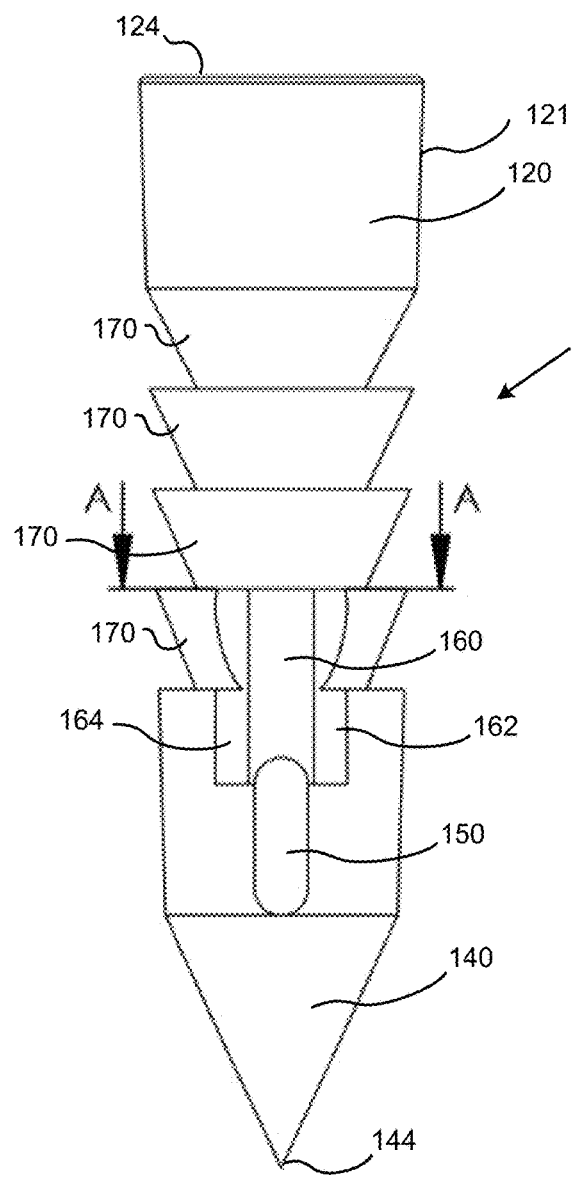
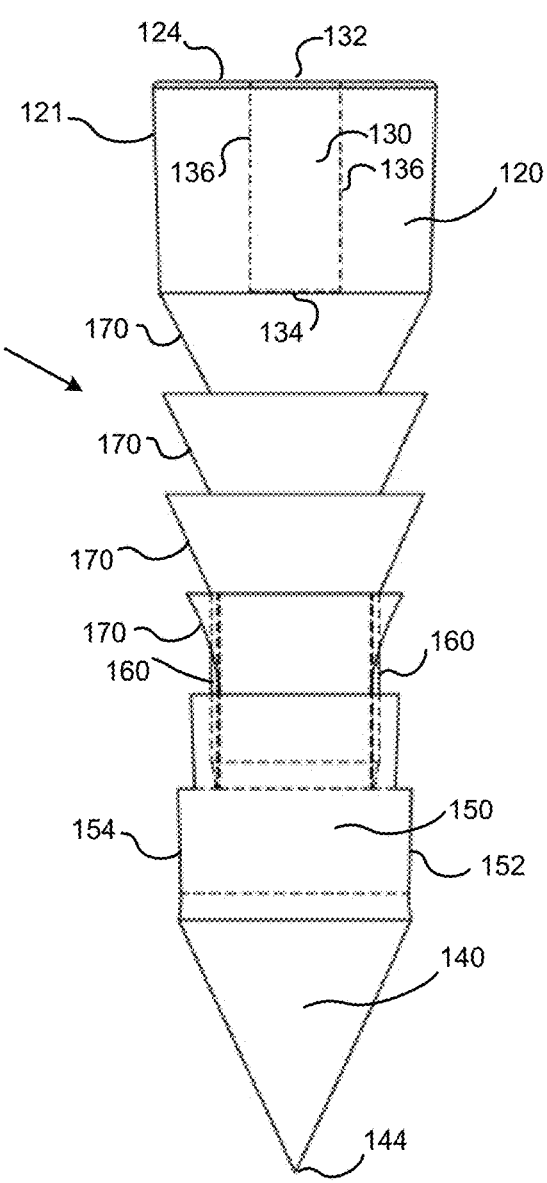
FIG. 2A
FIG. 2B

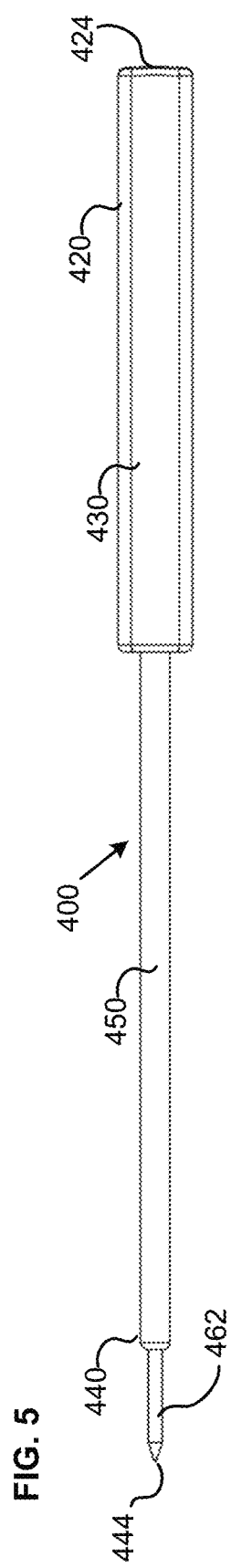
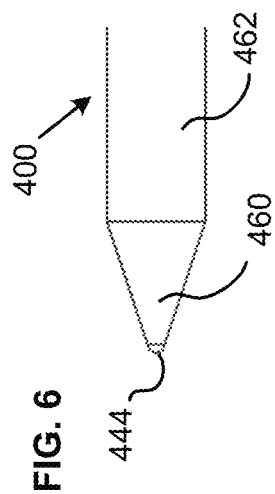

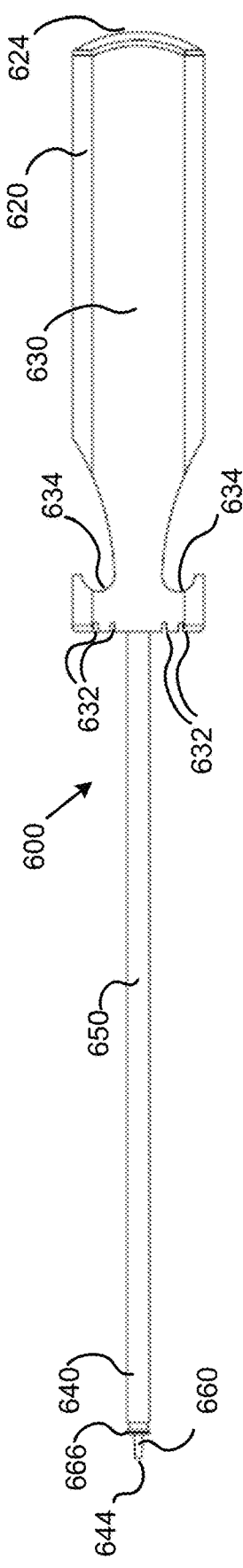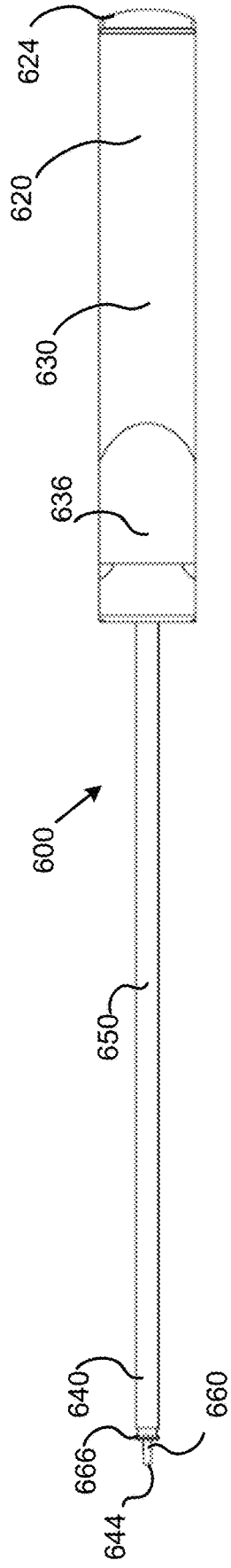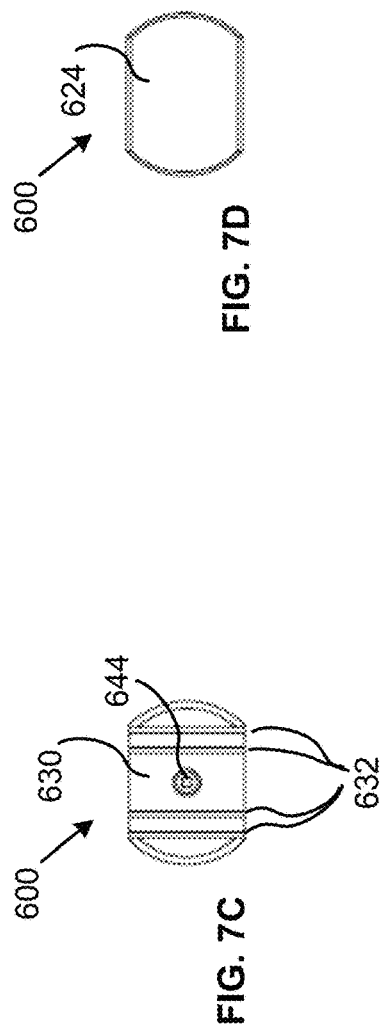
FIG. 7A
FIG. 7B
FIG. 7C
FIG. 7D

SUTURE ANCHORS AND METHODS OF USE

TECHNICAL FIELD

The present invention relates to a medical implant. More specifically, the present invention relates to an anchor system for securing tissue to bone.

BACKGROUND

Suture anchors are small medical devices that are used to fix tendons and ligaments to bone. The suture anchor, or anchor, is inserted into the bone and may include a screw mechanism and/or an interference fit design component.

Anchors are commonly used in rotator cuff tendon repair, biceps tendon repair, labral repair, and general shoulder instability repair. Current suture anchors are manufactured from metal and resorbable polymers. Suture anchors are usually laced with the desired suture and then inserted into a pilot hole in the bone using a hand-held inserter. Most surgical procedures involving the use of suture anchors are done arthroscopically. Additional equipment for such procedures may include appropriately sized awls, suture lassos, suture passers, and cannula for surgical access points.

SUMMARY

The needs set forth herein as well as further and other needs and advantages are addressed by the present teachings, which illustrate solutions and advantages described below.

It is an objective of the present teachings to remedy the above drawbacks and issues associated with the prior art.

The present invention resides in on aspect in an anchor system for securing suture tissue to bone. The system includes an anchor having an elongated body comprising a polyaryletherketone (PAEK) polymer that has been selectively sintered in accordance with a CAD file having a geometric description of the anchor. The elongated body extends along a longitudinal axis between a proximal region terminating in a proximal end and a distal region terminating in a distal end configured for insertion into a hole in the bone. The anchor includes a socket at the proximal region of the elongated body. The socket has a socket length extending along the longitudinal axis from an opening at the proximal region. The socket defines a cross-section that has a width in a first dimension D1. The system further includes an inserter that extends along an axis and has a protrusion at a distal region thereof, the protrusion has a protrusion length extending along the axis from a base of the protrusion toward a distal tip of the protrusion. The protrusion is configured to matingly engage with the socket. The protrusion defines a cross-section that decreases progressively in width in the dimension D1 along the protrusion length distally from the base of the protrusion toward the distal tip of the protrusion.

In yet a further embodiment of the present invention, the protrusion cross-section becomes smaller progressively in width in a second dimension D2 along the protrusion length distally from the base of the protrusion toward the distal tip of the protrusion.

In yet a further embodiment of the present invention, a width of the protrusion in the dimension D1 at the base of the protrusion is less than a width of the opening of the socket in the dimension D1 as specified by the CAD file.

In yet a further embodiment of the present invention, a width of the protrusion in the dimension D2 at the base of the protrusion is less than a width of the opening of the socket in the dimension as specified by the CAD file.

In yet a further embodiment of the present invention, D1 is perpendicular to D2, and D1 and D2 are both perpendicular to the longitudinal axis of the elongated body.

In yet a further embodiment of the present invention the socket cross-section as specified by the CAD file remains substantially constant in a width in the dimension D1 distally from the opening of the socket along the socket length and the socket cross-section as specified by the CAD file remains substantially constant in a width in the second dimension D2 distally from the opening of the socket along the socket length.

In yet a further embodiment of the present invention, the width of the protrusion in the dimension D1 at the base of the protrusion is less than the width of the opening of the socket in the dimension D1 as specified by the CAD file by at least a dimensional tolerance associated with the selective laser sintering process of the PAEK polymer to form the anchor. The width of the protrusion in the dimension D2 at the base of the protrusion is less than the width of the opening of the socket in the second dimension D2 as specified by the CAD file by at least the dimensional tolerance associated with the selective laser sintering process of the PAEK polymer to form the anchor.

In yet another embodiment of the present invention, the width of the protrusion in the dimension D1 at the base of the protrusion is less than the width of the opening of the socket in the dimension D1 as specified by the CAD file by at least 0.25 mm, and the width of the protrusion in the dimension D2 at the base of the protrusion is less than the width of the opening of the socket in the dimension D2 as specified by the CAD file by at least 0.25 mm.

In yet another embodiment of the present invention, the width of the protrusion in the dimension D1 at the base of the protrusion is less than the width of the opening of the socket in the dimension D1 as specified by the CAD file by at least 0.50 mm, and the width of the protrusion in the dimension D2 at the base of the protrusion is less than the width of the opening of the socket in the dimension D2 as specified by the CAD file by at least 0.50 mm.

In yet a further embodiment of the present invention, the cross-section of the opening defines an equilateral quadrilateral.

In yet a further embodiment of the present invention, the anchor includes barbs disposed on an outer surface of the body and an eyelet for receiving suture extending transversely through the body.

In yet a further embodiment of the present invention, the inserter defines a shoulder at the base of the protrusion, and the shoulder abuts a proximal area of the anchor body when the protrusion is matingly engaged with the socket.

In yet a further embodiment of the present invention, the protrusion is configured so that a distal tip of the protrusion abuts a bottom of the socket when the protrusion is matingly engaged with the socket.

The present invention resides in another aspect in an anchor system for securing suture tissue to bone. The system includes an anchor having an elongated body comprising a polyetherketoneketone (PEKK) polymer selectively sintered in accordance with a CAD file having a geometric description of the anchor. The elongated body extend is along a longitudinal axis between a proximal region terminating in a proximal end and a distal region terminating in a distal end configured for insertion into a hole in the bone. An outer surface of the elongated body has a roughness of at least 500 Ra (μ-in). The anchor includes a socket at the proximal region of the elongated body. The socket has a socket length extending along the longitudinal axis from an opening at the proximal region. The socket defines a cross-section having a width in a first dimension D1. An inserter extends along an axis and has a protrusion at a distal region thereof. The protrusion has a protrusion length that extends along the axis from a base of the protrusion toward a distal tip of the protrusion. The protrusion is configured to matingly engage with the socket. The protrusion defines a cross-section that decreases progressively in width in the dimension D1 along the protrusion length distally from the base of the protrusion toward the distal tip of the protrusion.

In yet a further embodiment of the cross-section of the opening defines an equilateral quadrilateral.

In yet a further embodiment, the width of the protrusion in the dimension D1 at the base of the protrusion is less than a width of the opening of the socket in the dimension D1 as specified by the CAD file.

In yet a further embodiment, the width of the protrusion in the dimension D1 at the base of the protrusion is less than the width of the opening of the socket in the dimension D1 as specified by the CAD file by at least a dimensional tolerance associated with the selective laser sintering process of the PEKK polymer.

In yet a further embodiment of the present invention, the width of the protrusion in the dimension D1 at the base of the protrusion is less than the width of the opening of the socket in the dimension D1 as specified by the CAD file by at least 0.50 mm.

In yet a further embodiment of the present invention, the socket cross-section remains substantially constant in a width in the dimension D1 distally from the opening of the socket along the socket length.

BRIEF DESCRIPTION OF THE DRAWINGS

FIG. 2A is a front view of an anchor in accordance with one embodiment of the present invention.

FIG. 2B is a side view of the anchor shown in FIG. 2A.

FIG. 5 is a front view of an awl in accordance with one embodiment of the present invention.

FIG. 6 is a front view of an awl in accordance with one embodiment of the present invention.

FIG. 7A is a side view on an inserter in accordance with one embodiment of the present invention.

FIG. 7B is a front view of the inserter shown in FIG. 7A.

FIG. 7C is a bottom view of the inserter shown in FIG. 7A.

FIG. 7D is a top view of the inserter shown in in FIG. 7A.

DETAILED DESCRIPTION

Figure 1:
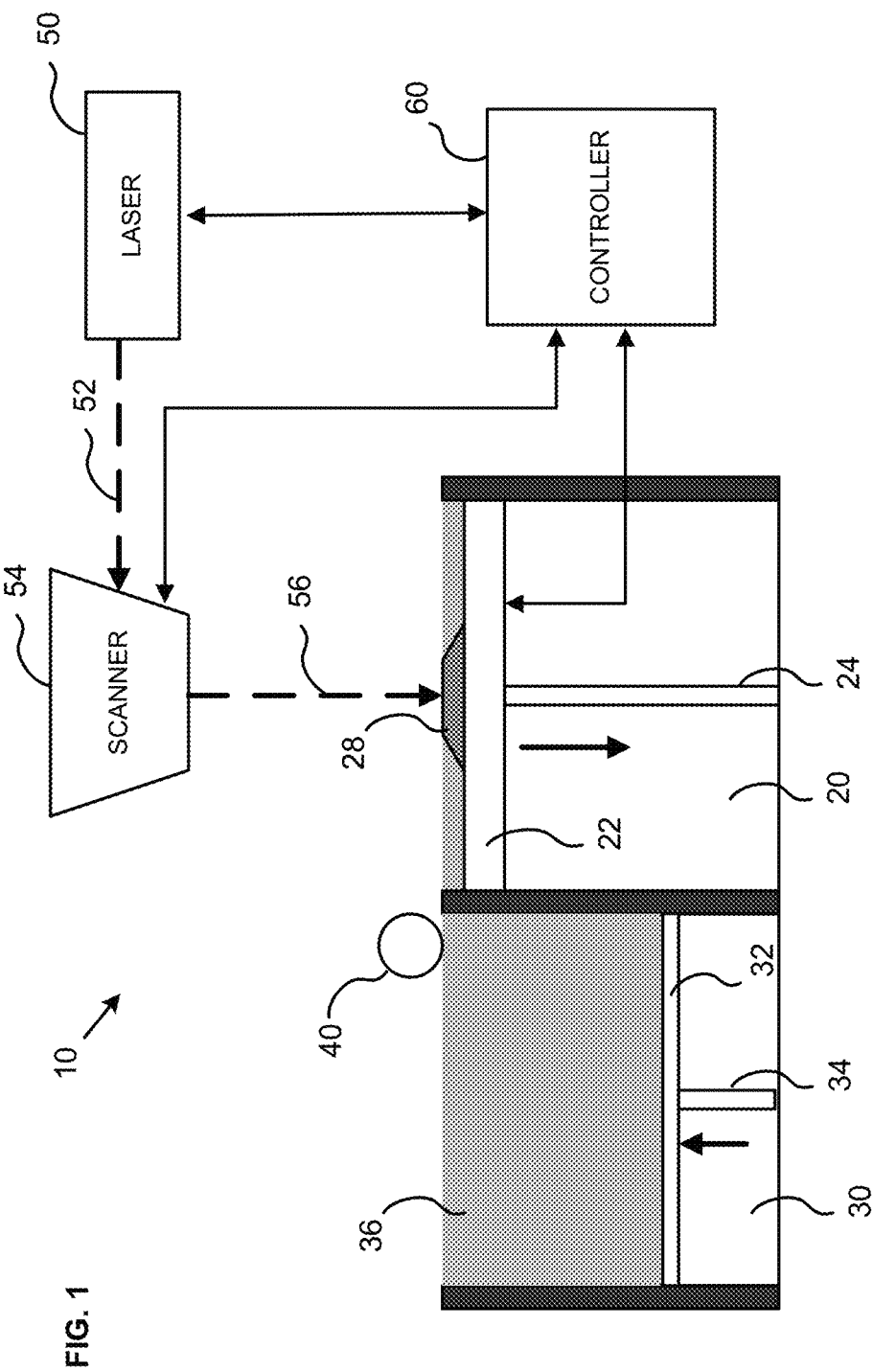
FIG. 1 is an illustration of a laser sintering machine in accordance with one embodiment of the present invention.
Figure 2C:
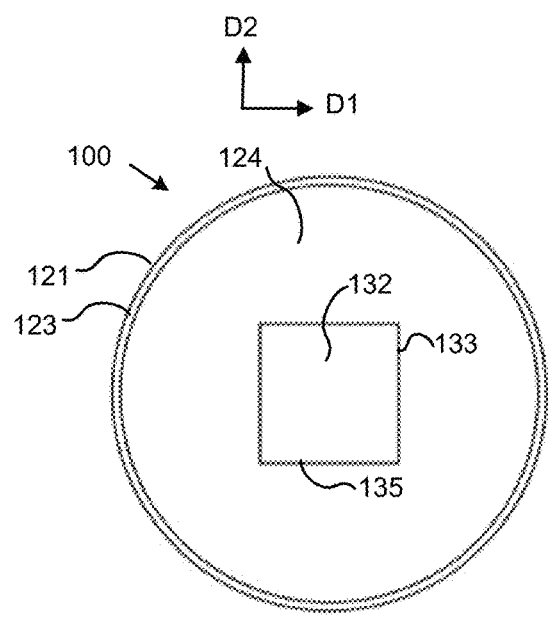
FIG. 2C is a top view of the anchor shown in FIG. 2A.
Figure 2D:
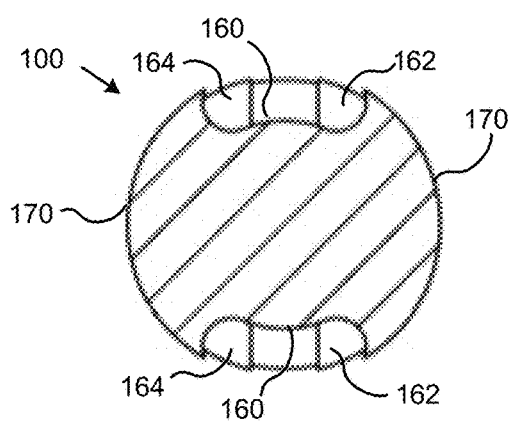
FIG. 2D is a cut-away view of the anchor shown in FIG. 2A along plane AA as illustrated in FIG. 2A.
Figure 2E:
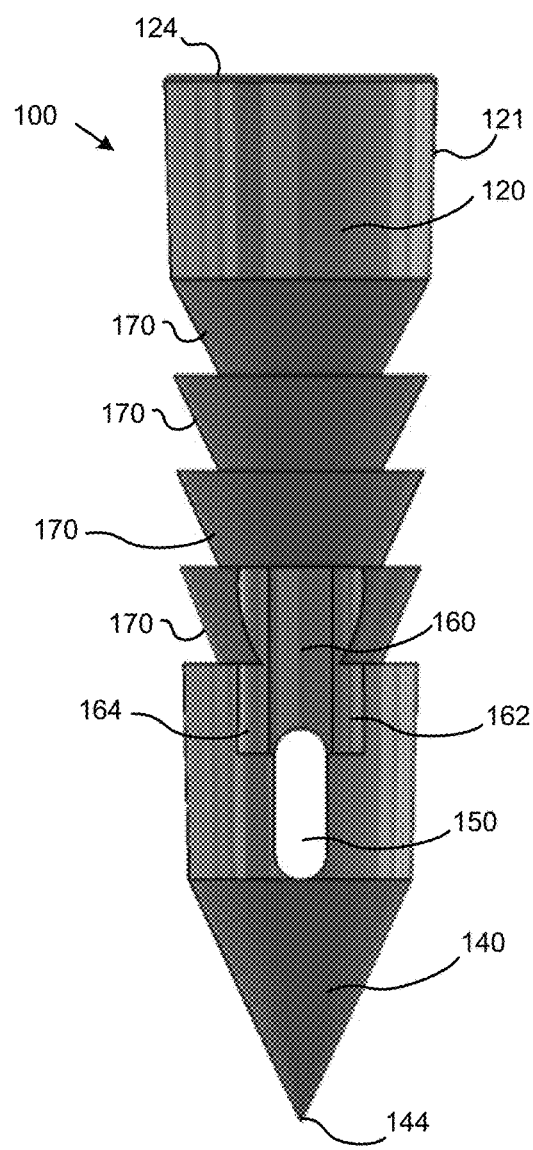
FIG. 2E is a front view of the anchor shown in FIG. 2A.

The present disclosure describes aspects of the present invention with reference to the exemplary embodiments illustrated in the drawings; however, aspects of the present invention are not limited to the exemplary embodiments illustrated in the drawings. It will be apparent to those of ordinary skill in the art that aspects of the present invention include many more embodiments. Accordingly, aspects of the present invention are not to be restricted in light of the exemplary embodiments illustrated in the drawings. It will also be apparent to those of ordinary skill in the art that variations and modifications can be made without departing from the true scope of the present disclosure. For example, in some instances, one or more features disclosed in connection with one embodiment can be used alone or in combination with one or more features of one or more other embodiments.

The present invention relates to anchor systems having anchors manufactured polymer powders by laser sintering. One such class of polymer powders is polyaryletherketones ("PAEK") polymers. PAEKs are of interest in the SLS process because parts that have been manufactured from PAEK powder or PAEK granulates are characterized by a low flammability, a good biocompatibility, and a high resistance against hydrolysis and radiation. The thermal resistance at elevated temperatures as well as the chemical resistance distinguishes PAEK powders from ordinary plastic powders. A PAEK polymer powder may be a powder from the group consisting of polyetheretherketone ("PEEK"), polyetherketoneketone ("PEKK"), polyetherketone ("PEK"), polyetheretherketoneketone ("PEEKK") or polyetherketoneetherketoneketone ("PEKEKK").

PEKKs are well-known in the art and can be prepared using any suitable polymerization technique, including the methods described in the following patents, each of which is incorporated herein by reference in its entirety for all purposes: U.S. Pat. Nos. 3,065,205; 3,441,538; 3,442,857; 3,516,966; 4,704,448; 4,816,556; and 6,177,518. PEKK polymers differ from the general class of PAEK polymers in that they often include, as repeating units, two different isomeric forms of ketone-ketone. These repeating units can be represented by the following Formulas I and II:

-A-C(=O)—B—C(=O)—　　　　I

-A-C(=O)—D—C(=O)—　　　　II where A is a p,p'-Ph-O-Ph-group, Ph is a phenylene radical, B is p-phenylene, and D is m-phenylene. The Formula I:Formula II isomer ratio, commonly referred to as the T:I ratio, in the PEKK is selected so as to vary the total crystallinity of the polymer. The T:I ratio is commonly varied from 50:50 to 90:10, and in some embodiments 60:40 to 80:20. A higher T:I ratio such as, 80:20, provides a higher degree of crystallinity as compared to a lower T:I ratio, such as 60:40.

The crystal structure, polymorphism, and morphology of homopolymers of PEKK have been studied and have been reported in, for example, Cheng, Z. D. et al, "Polymorphism and crystal structure identification in poly(aryl ether ketone ketone)s," Macromol. Chem. Phys. 197, 185-213 (1996), the disclosure of which is hereby incorporated by reference in its entirety. This article studied PEKK homopolymers having all para-phenylene linkages [PEKK(T)], one meta-phenylene linkage [PEKK(I)], or alternating T and I isomers [PEKK(T/I)]. PEKK(T) and PEKK(T/I) show crystalline polymorphism depending upon the crystallization conditions and methods.

In PEKK(T), two crystalline forms, forms I and II, are observed. Form I can be produced when samples are crystallized from melting at low supercooling, while Form II is typically found via solvent-induced crystallization or by cold-crystallization from the glassy state at relatively high supercooling. PEKK(I) possesses only one crystal unit cell which belongs to the same category as the Form I structure in PEKK(T). The c-axis dimension of the unit cell has been determined as three phenylenes having a zig-zag conformation, with the meta-phenylene lying on the backbone plane. PEKK(T/I) shows crystalline forms I and II (as in the case of PEKK(T)) and also shows, under certain conditions, a form III.

Suitable PEKKs are available from several commercial sources under various brand names. For example, polyetherketoneketones are sold under the brand name OXPEKK® polymers by Oxford Performance Materials, South Windsor, Connecticut. Polyetherketoneketone polymers are also manufactured and supplied by Arkema. In addition to using polymers with a specific T:I ratio, mixtures of polyetherketoneketones may be employed.

The powders used in these applications are produced by a variety of processes such as grinding, air milling, spray drying, freeze-drying, or direct melt processing to fine powders. The heat treatment can be accomplished before or after the powders are produced, but if treated prior to forming the powders, the temperature of the powder forming process must be regulated to not significantly reduce the melting temperature or the quantity of the crystallinity formed in the heat treatment process.

In regard to the embodiment using PEKK powder, a raw PEKK flake is provided. The raw PEKK flake is commercially available from companies such as Arkema, Inc. of King of Prussia, Pa., and Cytec Industries Inc. of Woodland Park, N.J.

A heat treatment step is optionally performed on the PEKK flake. The heat-treatment process is the subject of U.S. patent application Ser. No. 15/872,478 filed on Jan. 16, 2018 by Hexcel Corporation and titled "Polymer Powder and Method of Using the Same." The disclosure of that reference is hereby incorporated by reference. After the optional heating step, a grinding or milling step is performed that involves grinding the raw PEKK flake to form what will hereinafter be referred to as the "PEKK powder." The grinding step can be performed using known grinding techniques performed by companies such as Aveka, Inc. of Woodbury, Minn. Upon completion of the grinding step, the particles of the PEKK powder are significantly smaller (i.e., several degrees of magnitude smaller) than the particles of the raw PEKK. The particles of the PEKK powder are more consistent and regular in shape as compared to the particles of the raw PEKK; however, the particles of the PEKK powder are still irregularly-shaped in comparison to the spherical-shaped particles. A person of ordinary skill in the art and familiar with this disclosure will understand that the grinding may also be referred to as pulverization, milling, or jet milling. In addition, a person of ordinary skill in the art and familiar with this disclosure will understand that it may also be employed with other polymer powders, including those in the PAEK family.

The raw PEKK flake is ground into a PEKK powder comprising a plurality of PEKK particles. The PEKK particles range in size from less than 10 µm to about 200 µm. A person of ordinary skill in the art and familiar with this disclosure will understand that the particle size range will vary based on the type of polymer being milled and the specific parameters of the milling process. After the milling, an air classification method may be used to separate fine particles from the milled PEKK powder. It is known in the art that it is necessary to reduce or eliminate particles having a diameter below a cut-off point, for example 30 µm, as it has been found that particles in this range prevent use of the powder in the LS process. For example, International Patent Application WO2014100320 discloses such a method for preparing powders for use in selective laser sintering. It is understood in the art that parts cannot be manufactured in the SLS process from a powder wherein the fine particles have not been sieved from the powder. Such an unsieved powder causes pilling, sticking, and other forms of fouling in the powder application steps of the SLS process, and further results in curling and premature melting that inhibit use of such powders in the SLS process.

In some embodiments of the present invention a recycled polymer powder is used. Recycled PEKK material has previously been used in an SLS process but not formed into an object. The recycle process is the subject of U.S. Pat. No. 10,000,022 to Hexcel Corporation and titled "method for processing PAEK and articles manufactured from the same." The disclosure of that reference is hereby incorporated by reference.

According to one embodiment of the present invention, in reference to FIG. 1, a laser sinter ("LS") system 10 in accordance with the present invention is illustrated. The system 10 includes a first chamber 20 having an actuatable piston 24 deposed therein. A bed 22 is deposed at an end of the piston 24. It should be understood that the term bed may refer to the physical structure supported on the piston or the uppermost layer of powder deposed thereon.

The temperature of the bed 22 can be variably controlled via a controller 60 in communication with heating elements (not shown) in or around the bed 22. Furthermore, the LS system 10 according to the invention may include a heating device (not shown) above the bed 22, which preheats a newly applied powder layer up to a working temperature below a temperature at which the solidification of the powder material occurs. The heating device may be a radiative heating device (e.g., one or more radiant heaters) which can introduce heat energy into the newly applied powder layer in a large area by emitting electromagnetic radiation.

A second chamber 30 is adjacent to the first chamber 20. The second chamber 30 includes a table surface 32 disposed on an end of a piston 34 deposed therein. A powder 36 for use in the LS system 10 is stored in the second chamber 30 prior to the sintering step. It will be understood to a person of ordinary skill in the art and familiar with this disclosure that while a specific embodiment of a LS system is disclosed, the present invention is not limited thereto, and different known LS systems may be employed in the practice of the present invention.

During operation of the LS system 10, a spreader 40 translates across a top surface of the first chamber 20, evenly distributing a layer of powder 36 across onto either the top surface of the bed 22 or the material previously deposed on the bed 22. The LS system 10 preheats the powder material 36 deposed on the bed 22 to a temperature proximate to a melting point of the powder. Typically, a layer of powder is spread to have a thickness of 125 μm, however the thickness of the layer of powder can be increased or decreased depending on the specific LS process and within the limits of the LS system.

A laser 50 and a scanning device 54 are deposed above the bed 22. The laser 50 transmits a beam 52 to the scanner 54, which then distributes a laser beam 56 across the layer of powder 36 deposed on the bed 22 in accordance with build data. The build data comprises a computer-aided design ("CAD") file having a geometric description of the object that is being built. The laser selectively fuses powder material by scanning cross-sections generated from a three-dimensional digital description of the part on the surface of the bed having a layer of the powder material deposed thereon. The laser 50 and the scanner 54 are in communication with the controller 60. After a cross-section is scanned, the bed 22 is lowered by one-layer thickness (illustrated by the downward arrow), a new layer of powdered material is deposed on the bed 22 via the spreader 40, and the bed 22 is rescanned by the laser. This process is repeated until a build 28 is completed. During this process, the piston 34 in the second chamber is incrementally raised (illustrated by the upward arrow) to ensure that there is a sufficient supply of powder 36.

Parts made from the SLS process have a dimensional tolerance of between 0.2 mm and 0.5 mm plus or minus a specified dimensional value as set forth in the CAD file having a geometric description of the object. It will be understood to a person of ordinary skill in the art and familiar with this invention that the term CAD file having a geometric description of the object includes any set of electronic instructions for the SLS machine to print an object with a specified geometry.

The ±0.3 to ±0.5 mm dimensional tolerance associated with SLS is caused by several different factors associated with SLS. First, as the object cools after the printing job it typically contracts and shrinks. It is possible to account for this shrinkage by adjusting the geometric description of the object in the CAD file. Nevertheless, some variance in the dimensional tolerance is likely. A second cause of the dimensional tolerance is that the polymer powder in the build chamber adjacent to sintered object may inadvertently adhere to the surface of the object as a result of incidental melting or incidental particle adhesion due to the thermal conductivity of the adjacent sintering source. This effect is seen on the up skin and down skin surfaces, an on the z-plane surfaces. Another factor that affects the dimensional tolerance associated with the SLS of polymers is the subsequent buildup up of layers that form the objects.

The anchor system in accordance with one embodiment includes an anchor, an awl, and an inserter. In reference to FIGS. 2A-2E, an anchor 100 in accordance with one embodiment of the present invention is shown. The anchor 100 is manufactured from PEKK powder using the above described LS printing method using a CAD file having a geometric description of the anchor 100.

The anchor 100 has an elongated body that extends along a longitudinal axis between a proximal region 120 terminating in a proximal end 124 and a distal region 140 terminating in a distal end 144. In the embodiment shown in the FIGS. the axis is linear, however the present invention is not limited in this regard and a person or ordinary skill in the art and familiar with this disclosure will understand that other configurations may be possible.

FIGS. 2A-2E illustrate a geometric description of the anchor in accordance with the specified geometry. It will be understood by a person of skill in the art and familiar with this disclosure that an anchor printed from a polymer via the SLS process in accordance with the specified geometry will have a dimensional tolerance associated with the polymer and the conditions of the SLS process. For example, in the case of SLS of PEKK powder the dimensional tolerance is between ±0.3 mm ±0.5 mm depending on the position of the printed object in the build chamber and further depending on the geometry of the printed part.

An outside surface 121 of the anchor 100 defines a convex arcuate surface in a plane perpendicular, or orthogonal, to the longitudinal axis of the body 100. In the embodiment disclosed in FIGS. 2A-2E, the outer surface 121 defines a circular cross-section in the plane being perpendicular to the longitudinal axis. The distal region 140 of the anchor 100 terminates in a distal end 144 that is configured for insertion into bone. In one type of procedure for which the anchor may be used, an initial hole is formed in the bone via an awl. A distal tip 144 of the anchor 100 is then inserted into the hole.

The anchor 100 has an eyelet 150 that extends transversely through the anchor perpendicular to the longitudinal axis of the anchor 100. The eyelet 150 extends through the body 100 between a first opening 152 and a second opening 154. During use of the anchor 100, suture is received through the eyelet 150 prior to insertion of the anchor into bone. The anchor 100 includes channels 160 in the surface 121 on opposing sides of the that extend proximally from eyelet 150. Each channel 160 is defined by opposing walls 162, 164 that extend between a bottom of the channel 160 and the surface 121 of the anchor 100. The anchor 100 includes a plurality of barbs 170 on the outer surface 121. The barbs 170 are configured to retain the anchor 100 in the bone after insertion. It will be understood by a person of skill in the art and familiar with this disclosure that provision of barbs 170 and the number thereof may vary. In some embodiments, for example, the anchor does not include barbs. In yet other embodiments, the outer surface of the anchor defines a helical screw such that the anchor may be rotated into the bone.

The anchor 100 has a socket 130 at the proximal region 120. The socket 130 is configured to matingly engage with a protrusion 660 of an inserter 600. The socket 130 defines an opening 132 and has a length that extends along the longitudinal axis of the anchor 100 from the opening 132 at the proximal region 120. The socket 130 defines a cross-section in a plane perpendicular to the longitudinal axis. The socket 130 has a width in a first direction D1. In the embodiment shown in FIGS. 2A-2E, D1 is perpendicular to the longitudinal axis. The socket 130 has a width in a second direction D2. In the embodiment shown in FIGS. 2A-2E, D2 is perpendicular to the longitudinal axis and perpendicular to D2, such that D1 and D2 define a plane that is orthogonal to the longitudinal axis. This disclose refers to an inserter 600 that extends along a longitudinal axis and anchor extending along an axis. The disclosure further refers to a first direction D1 and a second direction D2 in reference to the anchor and in reference to the inserter. The first direction D1 for the anchor is also the first direction D1 for the inserter when the longitudinal axis of the anchor is parallel to the longitudinal axis of the inserter. The second direction D2 for the anchor is also the second direction D2 for the inserter when the longitudinal axis of the anchor is parallel to the longitudinal axis of the inserter.

In the embodiment shown in FIGS. 2A-2E, the socket 130 cross-section as specified by the CAD file remains substantially constant in the width in the first dimension D1 distally from the opening 132 of the socket along the socket length. The socket 130 cross-section as specified by the CAD file remains substantially constant in a width in the second dimension D2 distally from the opening 132 of the socket along the socket length. In the embodiment disclosed in FIGS. 2A-2E, the width of the cross-section in the dimension D1 and D2 is substantially constant from the length extending from opening 132 to a bottom 134 of the socket 130.

In the embodiment disclosed, the cross-section of the socket 130 defines an equilateral quadrilateral at the opening 132 and the base 134. In other embodiments of the present invention, the cross-section defines a quadrilateral. That inventors have discovered that employing the quadrilateral cross-section in the socket 130 and a corresponding cross-section of the mating protrusion 660, the system enables the surgeon to obtain an engagement between the inserter 600 and the anchor 100 to provide smooth transmission of force along the axis of the engagement and laterally thereto to ensure proper insertion of the anchor into the bone. Moreover, this configuration provides relative ease in retraction of the inserter from the anchor after insertion thereof. As will be described below, the proposed engagement in accordance with the present invention addresses the dimensional tolerances associated with the SLS process. A person of ordinary skill in the art and familiar with this disclosure will understand that additional cross-section shapes may be possible with the present invention, such as hexagons and triangular. The anchors in accordance with the present invention are available in different sizes enabling use on different areas of the body or on different size patients. In FIGS. 2A-2B, the anchor 100 is approximately 6.5 mm in diameter in a cross-section at a proximal region 120 thereof.

Figure 3:
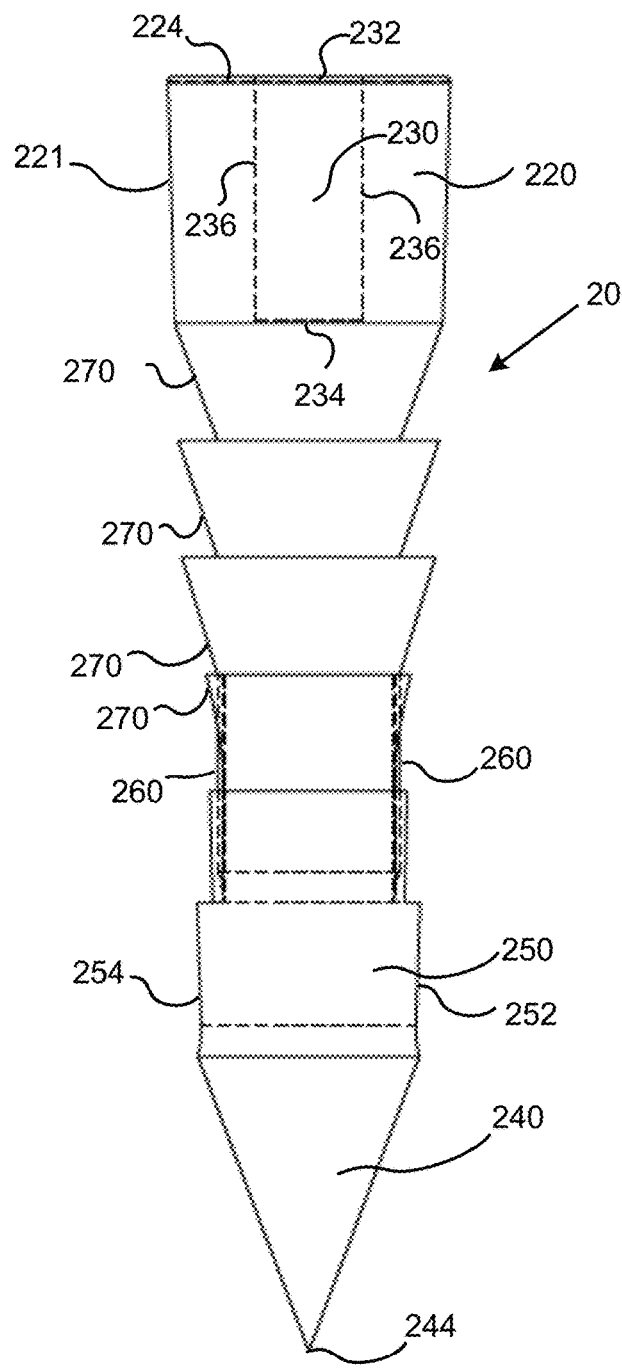
FIG. 3 is a side view of an anchor in accordance with one embodiment of the present invention.
Figure 4:
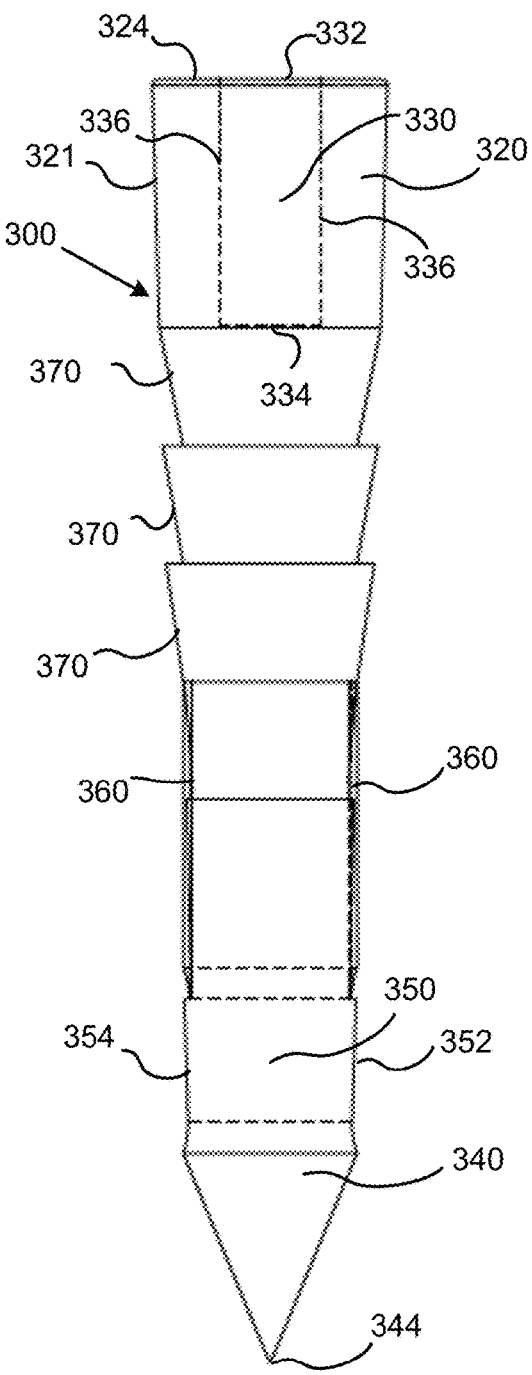
FIG. 4 is a side view of an anchor in accordance with one embodiment of the present invention.

In reference to FIGS. 3 and 4, two additional anchors 200, 300 in accordance with the present invention are illustrated. The anchor 200 is approximately 5.5 mm in diameter in a cross-section at a proximal region 220 thereof. The anchor 300 is approximately 4.5 mm in diameter in a cross-section at a proximal region 320 thereof. The anchor 200, 300 has an elongated body 200, 300 that extends along a longitudinal axis between a proximal region 220, 320 terminating in a proximal end 224, 324 and a distal region 240, 340 terminating in a distal end 244, 344. FIGS. 3 and 4 illustrate a geometric description of the anchor in accordance with the specified geometry. The actual dimensions of the objected printed from SLS may vary within the dimensional tolerance associated with the SLS process and the selected material.

An outside surface 221, 321 of the anchor 200, 300 defines a convex arcuate surface in a plane perpendicular to the longitudinal axis of the body 200, 300. The outer surface 221, 321 defines a circular cross-section in a plane perpendicular to the longitudinal axis. The distal region 240, 340 of the anchor 200, 300 terminates in a tip 244, 344 configured for insertion into bone.

The anchor 200, 300 has an eyelet 250, 350 that extends transversely through the anchor perpendicular to the longitudinal axis of the anchor. The eyelet 250, 350 extends through the body 200, 300 between a first opening 252, 352 and a second opening 254, 354. During use of the anchor 200, 300, suture is received through the eyelet 250, 350 prior to insertion of the anchor into the bone. The anchor 200, 300 includes a channel 260, 360 in a surface thereof that extends proximally from eyelet 250, 350 on opposing sides of the anchor 200, 300. The channel 260, 360 is further defined by opposing walls that extend between a bottom of the channel 260, 360 and an outside surface of the anchor 200, 300. The anchor 200, 300 includes a plurality of barbs 270, 370 on the outer surface of the body 200, 300.

The anchor 200, 300 has a socket 230, 330 at the proximal region 220, 320 of the elongated body 200, 300. The socket 230, 330 is configured to matingly engage with a protrusion of an inserter. The socket 130 defines an opening 232, 332 and has a length that extends along the longitudinal axis of the anchor 200, 300 from the opening 232, 332 at the proximal region 220, 320. The socket 230, 330 defines a cross-section in a plane perpendicular to the longitudinal axis. The socket 230, 330 extends from the opening 233, 332 along a length to a bottom 234, 334. An inside surface 236, 336 defines an inside surface of the socket 230, 330.

In FIGS. 5A, 6, an awl 400 is shown. The awl 400 is used to create a pilot hole in the bone into which the anchor is inserted. The awl 400 extends along an axis from a proximal end 424 at a proximal region 420 to a distal tip 444 at a distal region 440. The awl includes a handle 430 at the proximal region 420. The handle 430 includes a strike plate at the proximal end 424. The awl 400 has tip 444 at the distal region that extends distally from a shaft 462 for insertion in the bone. The shaft 462 tapers at it extends distally to form the tip 444. A secondary shaft extends between the handle 430 and the shaft 462 for insertion. During use in a surgical procedure, the awl 400 is used to create a pilot hole in the bone for the anchor by lightly malleting the strike plate on the distal end 424 of the awl 400.

The awl 400 has a diameter at the insertion tip 462 that corresponds with the designated anchor diameter for insertion. For example, the 6.5 diameter anchor has a larger diameter awl associated therewith, while the smaller diameter anchor has a smaller diameter awl associated therewith. In some procedures, the surgeon may select a smaller or larger than normal awl for an associated suture anchor to provide a specific fit based on the anatomy, type of procedure, or some other factor. It should be understood to a person of ordinary skill in the art and familiar with this disclosure that different types of awls may be used in association with the present invention. In other embodiments, another method may be used.

In reference to FIGS. 7A-7D, 8A-8B, and 9A-9B an inserter in accordance with the present invention is shown. The inserter 600 is configured to matingly engage with the anchor 100. A protrusion 660 is received in the socket 130 when the protrusion is fully received in the socket. A distal tip 644 of the protrusion 660 abuts a bottom 134 of the socket and a collar 666 of the inserter abuts a proximal end 124 of the anchor when the protrusion is fully received in the socket.

During use, the surgeon can receive suture affixed to tissue via the anchor and insert the anchor into the bone. The mating engagement between the anchor and the inserter enables the surgeon to control the position of the anchor inside the body via a handle on a proximal end of the inserter that is outside the body. Tensioning of the suture and insertion of the anchor is an intricate procedure that requires precision. The engagement between the inserter and the anchor must allow for smooth and efficient transmission of force along the axis of the engagement to facilitate insertion of the anchor into the patient. The engagement should also permit an axial transmission of force so that if the inserter is rotated about its axis this rotational force is transmitted to the suture anchor. Likewise, the engagement should permit a lateral application of force from the inserter to the anchor. Finally, the engagement between the anchor and the inserter should allow for the surgeon to retract the inserter from the engagement with the anchor after the anchor has been inserted into the bone, while retaining the anchor in the bone.

Use of the selective laser sintering technique with a polymer powder to print anchors is complicated by the relatively small size of the anchors and the dimensional tolerance of the SLS process. It inhibits use of known engagements due to the variance in the dimensional tolerance associated with the selective laser sintering process. The interior dimensions of the socket in the printed anchor vary within the associated dimensional tolerance. In the case of suture anchors, this variance is particularly challenging because it can vary between 0.3 mm and 0.5 mm and the diameter of the suture anchors can be a small 4.5 mm.

The inventors have conceived, tested and developed an engagement that addresses these disadvantages associated with the variance of the dimensional tolerance and that provides satisfactory force transmission while also providing smooth retraction of the inserter after full insertion of the anchor. As discussed in reference to the embodiment above, the socket has a width in the first dimension D1 as defined by the CAD file having a geometric description of the object and a width in a second dimension D2 as defined by the CAD file. In order to account for the dimensional tolerance, the inserter 600 in accordance with one embodiment of the present invention has a cross-section that can be received in the socket 132.

In the embodiment disclosed in FIGS. 7A-7D, 8A-8B, and 9A-9B, a greatest width of the inserter in the dimension D1 is less than the width of the socket in the dimension D1. Likewise, the greatest width of the inserter in the dimension D2 is less than the width of the socket in the dimension D2. In some embodiments, the protrusion cross-section becomes smaller progressively in width in the first dimension D1 and the second dimension D2 along the protrusion length distally from the base of the protrusion toward the distal tip of the protrusion. In some embodiments, the width of the protrusion in the dimension D1 at the base of the protrusion is less than the width of the opening of the socket in the dimension D1 as specified by the CAD file by at least a dimensional tolerance associated with the selective laser sintering process of the polymer to form the anchor. Likewise, the protrusion in the dimension D2 at the base of the protrusion is less than the width of the opening of the socket in the second dimension D2 as specified by the CAD file by at least the dimensional tolerance associated with the selective laser sintering process of the polymer to form the anchor. In this manner, it is possible to provide a mating engagement between the inserter in the anchor printed from a polymer via SLS wherein the surgeon can transfer the necessary forces across the engagement and retract the inserter from the socket after the insertion of the anchor into the bone tissue.

In reference to FIG. 7A-7D, an inserter 600 in accordance with one embodiment of the present invention is disclosed. The inserter 600 extends along an axis from a proximal region 620 defining a proximal end 624 to a distal region 640 defining a distal end 644. The inserter 600 has a handle 630 at the proximal region 620. A surgeon or other person can manipulate the inserter 600 via the handle 630. The inserter 600 includes a protrusion 660 at the distal region 640 that extends from a base 664 to the distal tip of the protrusion 600, which is also the distal tip of the inserter 600. A shaft 650 extends along the axis between the handle 630 and the protrusion 660. In the embodiment shown in FIG. 7, the shaft 650 has a circular cross-section however, the present invention is not limited in this regard, as the shaft may have a different shaped cross-section including an oval, a quadrilateral, or some other shape. In the embodiment shown in FIG. 7, the inserter 600 is manufactured from stainless steel through a manufacturing process that has a dimensional tolerance of approximately plus or minus 0.1 mm, although a person of skill in the art will understand that it is possible to reduce this dimensional tolerance to 0.03 mm with stainless steel.

The handle 630 includes a first recess 636 and a second recess 636 on an opposing side at a location remote from the proximal end 624 of the inserter 600. The recesses 636 are configured to receive suture extending from the body. The surgeon can wrap an end of the suture on a cleat 634. The suture can be retained on one of several indentions 634 provided in a distal face of the handle 633 thereby retaining a separation of the suture during installation of the anchor. It will be understood to a person of skill in the art and familiar with this disclosure that alternative handle configurations and methods for tensioning and retaining suture tension may be employed with the present invention.

Figure 8A:
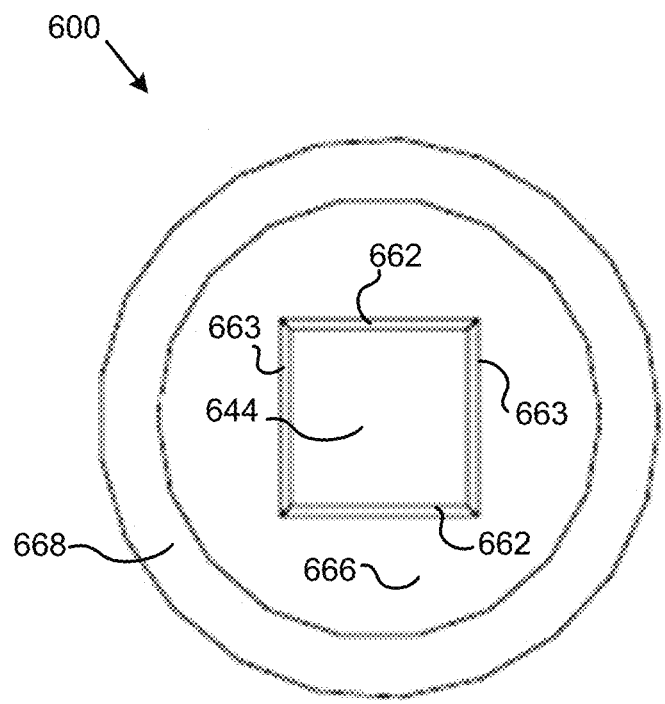
FIG. 8A is a bottom view of an inserter in accordance with one embodiment of the present invention.
Figure 8B:
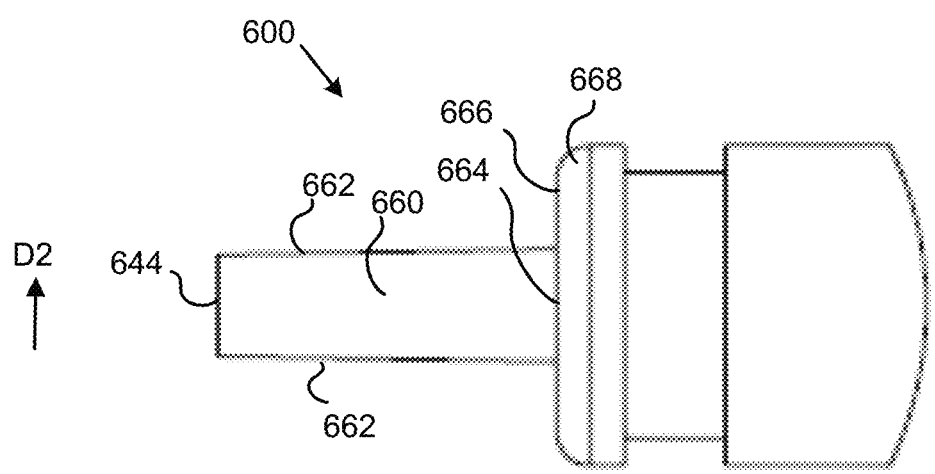
FIG. 8B is a front view of a portion of an inserter shown in FIG. 8A.

In FIGS. 8A and 8B a portion of the inserter 600 is shown. The protrusion 660 extends from a base 664 to a distal end 644. In reference to FIG. 8A, the protrusion defines a square cross-section in a plane perpendicular to the axis of the handle. The distal tip 644 of the protrusion defines a generally planar surface being perpendicular to the axis of the inserter 600. The protrusion 660 disclosed in this embodiment includes opposing sides 662 and opposing sides 663 that extend from the base of the protrusion to the distal end 644 of the protrusion. The inserter 600 defines a shoulder 666 between the protrusion 660 and the shaft 650. The shoulder 666 defines a rounded section 668 around a periphery thereof.

The protrusion 660 is tapered from its base 664 toward the distal tip 644 of the protrusion. The taper facilitates a mating engagement with the socket 130. In reference to the embodiment shown in FIG. 9A-9B, the protrusion 660 defines a cross-section that decreases progressively in width in the dimension D1 and the dimension D2 along the protrusion length distally from the base 664 of the protrusion toward the distal tip 644 of the protrusion.

Figure 9A:
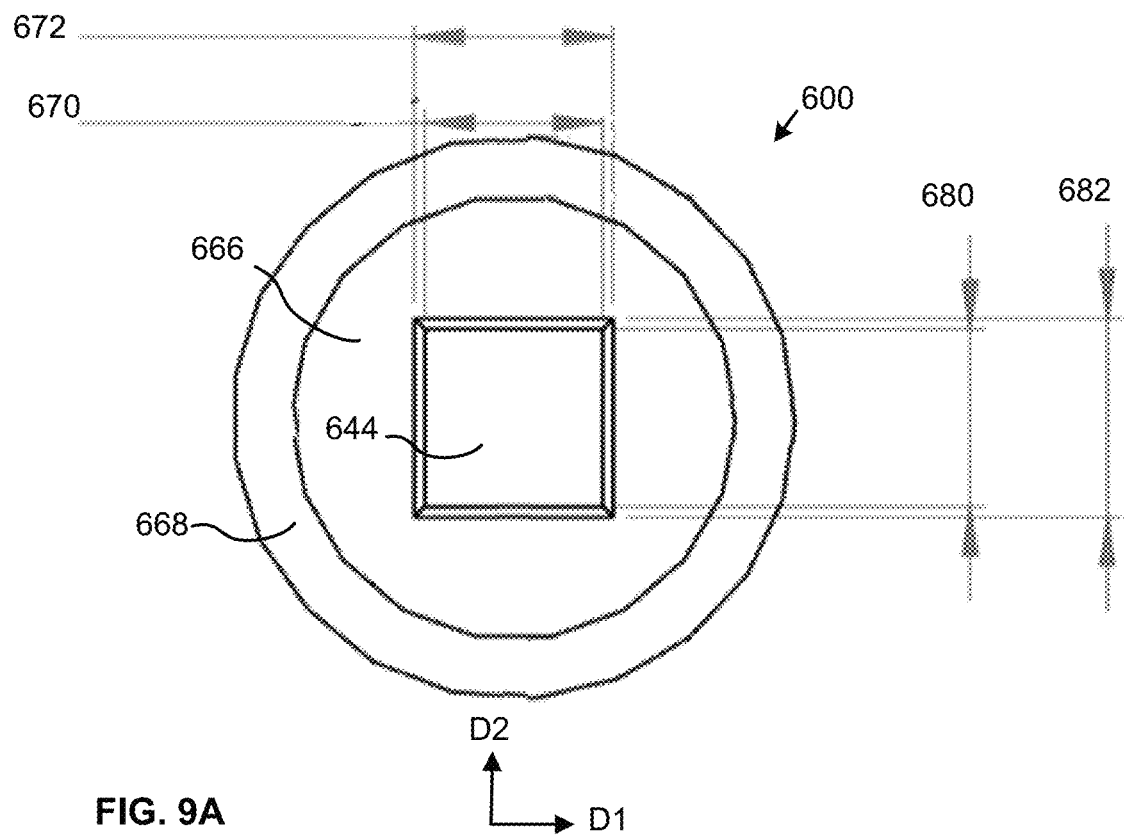
FIG. 9A is a bottom view of an inserter in accordance with one embodiment of the present invention.
Figure 9B:
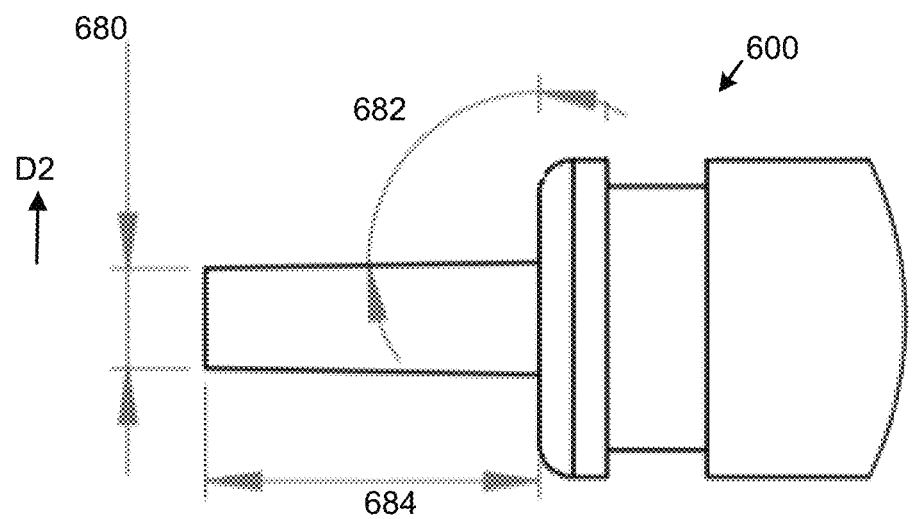
FIG. 9B is a front view of a portion of an inserter shown in FIG. 9A.

In the embodiment disclosed in FIGS. 9A and 9B, the protrusion 660 defines an equilateral quadrilateral in a plane being orthogonal to the axis of the inserter 600. The protrusion 660 has a width 672 in a first dimension D1 at the base 664 of the protrusion. The first dimension D1 is perpendicular to the axis of the inserter 600. The width of the protrusion 660 in the first dimension D1 progressively decreases from a base 664 of the protrusion to the distal tip 644 of the protrusion. The protrusion 600 has a width 670 in the in the first dimension at the distal tip 644 of the protrusion. The width of the protrusion 660 at the base in the first dimension D1 672 is greater than the width of the protrusion at the distal tip in the first dimension D1 670. As discussed, the width deceases in the first dimension D1 from the base 664 to the distal tip 644.

The protrusion 660 has a width 682 in a second dimension D2 at the base 664 of the protrusion 660. The second dimension D2 is perpendicular to the axis of the inserter 600. The width of the protrusion 660 in the second dimension D2 progressively decreases from a base 664 of the protrusion to the distal tip 644 of the protrusion. The protrusion has a width 680 in the in the second dimension D2 at the distal tip 644 of the protrusion. The width of the protrusion 660 at the base 664 in the second dimension D2 682 is greater than the width of the protrusion at the distal tip 644 in the second dimension D2 680. The width of the protrusion deceases in the second dimension D2 from the base 664 to the distal tip 644 along the length 684 of the protrusion.

A shoulder 666 extends from the base 664 of the protrusion 660 radially outward in the plane perpendicular to the axis of the inserter. In the disclosed embodiment, the surface 662 of the protrusion 660 extends in a plane that forms an angle with the shoulder that is greater than 90 degrees. This results in the taper of the inserter.

The width 672 of the protrusion in the dimension D1 at the base 664 of the protrusion is less than a width of the opening of the socket 130 in the dimension D1 as specified by the CAD file. In the embodiment disclosed, the width 672 is 1.68 mm and the width of the opening of the socket 130 in the dimension D1 as specified by the CAD file is 2.10 mm. The width 670 of the protrusion in the dimension D1 at the distal tip 644 of the protrusion 660 is 1.50 mm and the width of the socket 130 in the dimension D1 as specified by the CAD file is 2.10 mm. The face 663 forms an angle with the shoulder 666 that is 91.03°.

The width 682 of the protrusion in the second dimension D2 at the base 664 of the protrusion 660 is less than a width of the 132 opening of the socket 130 in the second dimension D2 as specified by the CAD file. In the embodiment disclosed, the width 682 is 1.68 mm and the width of the opening of the socket 130 in the dimension D2 as specified by the CAD file is 2.10 mm. The width 680 of the protrusion in the dimension D2 at the distal tip 644 of the protrusion 660 is 1.50 mm and the width of the socket 130 in the dimension D2 at its base as specified by the CAD file is 2.10 mm. The face 663 forms an angle with the shoulder 666 that is 91.03°. In some embodiments, the width of the protrusion in the first dimension or the second dimension is less than the width of the opening by a dimensional tolerance associated with the SLS.

Figure 11:
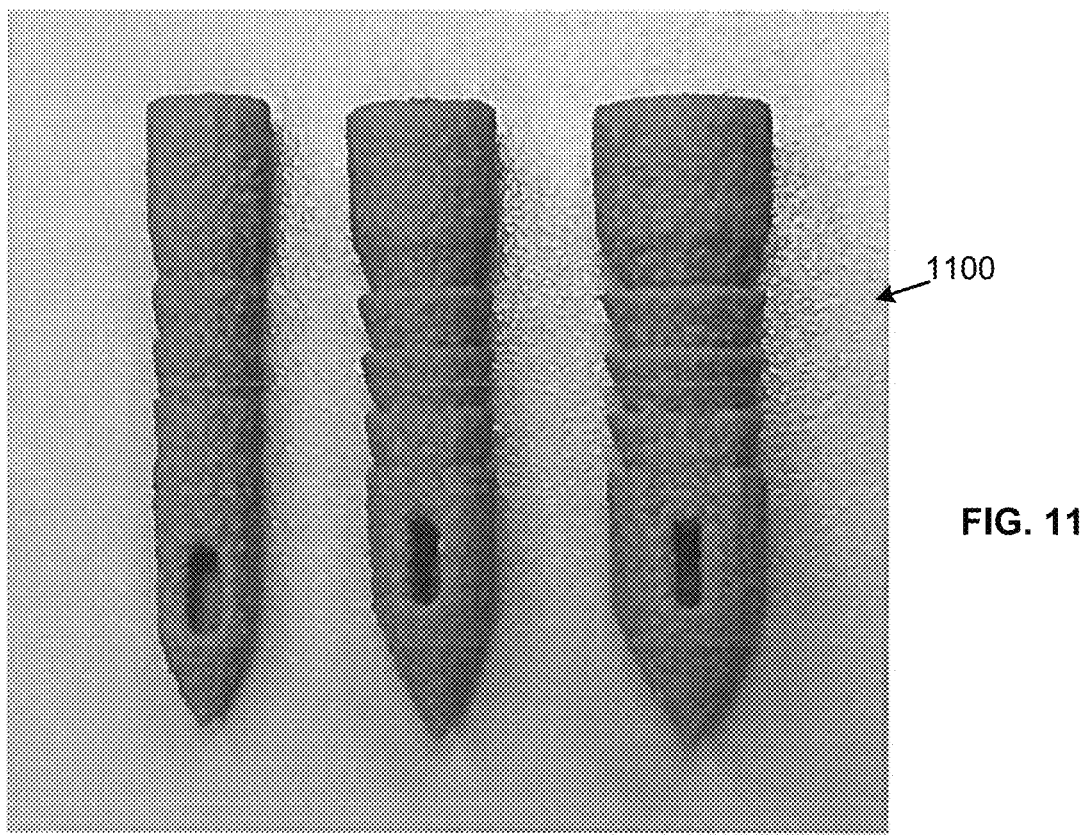
FIG. 11 is an image showing three anchors in accordance with the present invention.

In reference to FIG. 11, three anchors manufactured from PEKK using SLS are shown. The extensive surface roughness of anchors is evident. The inventors have discovered that while the dimensional tolerance affects the technical issue of inserter engagement it also enhances osteogeneration between the hard tissue surrounding the implant and the implant. In order to quantify the surface roughness of the anchors in accordance with the present invention, the applicants produced 90 test specimens in the xy-direction in an SLS printing machine using PEKK powder that was either virgin or recycled. The specimens comprised blank rectangular test parts. Another 90 test specimens were printed in the Z-direction using SLS from the same PEKK powder lots. After the test specimens were printed the surface roughness was measured. The surface roughness averaged 623.18 Ra (pin) on the xy-surface, or in-plane surface, and 1069.7 Ra (pin) on the Z-surface, or out of plane surface.

Figure 10A:
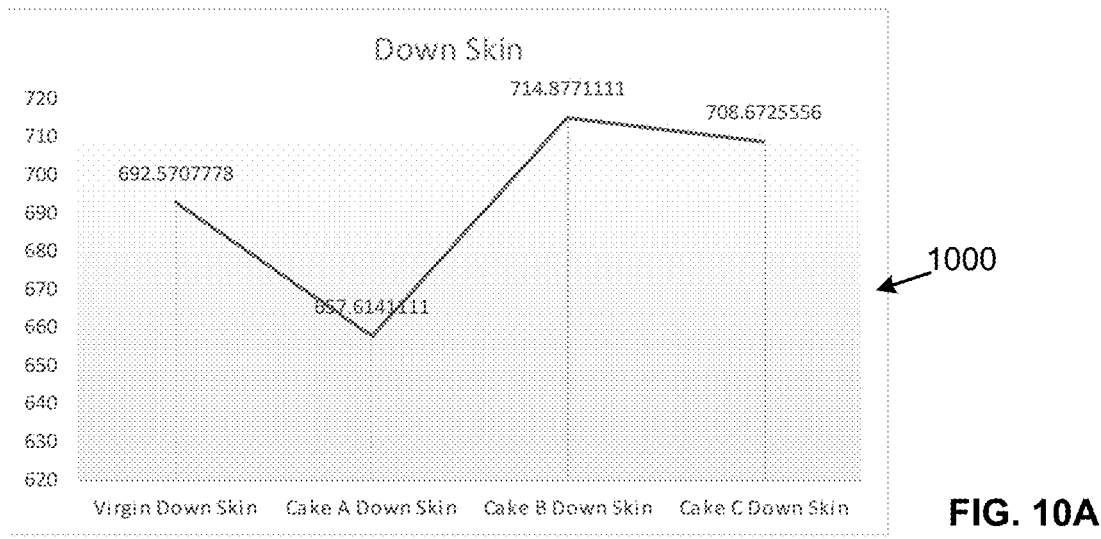
FIG. 10A is a chart showing surface roughness of a down skin surface of an anchors in accordance with the present invention.
Figure 10B:
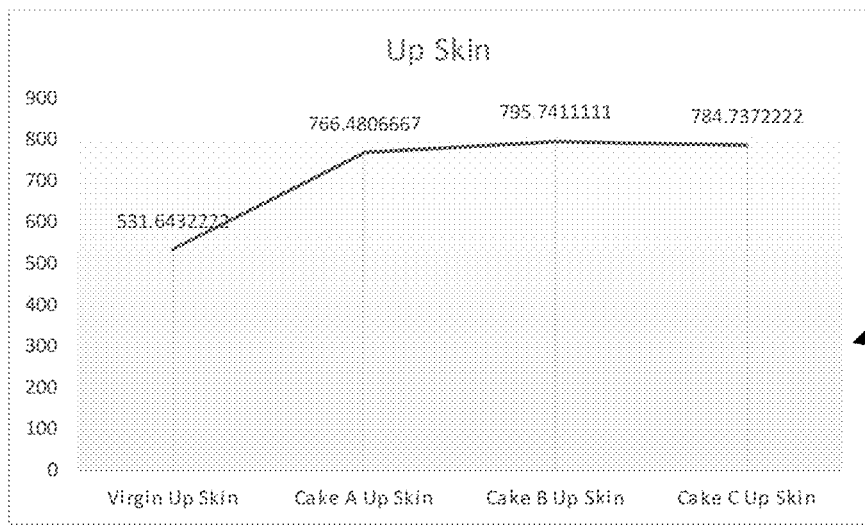
FIG. 10B is a chart showing surface roughness of an up skin surface of an anchors in accordance with the present invention.
Figure 10C:
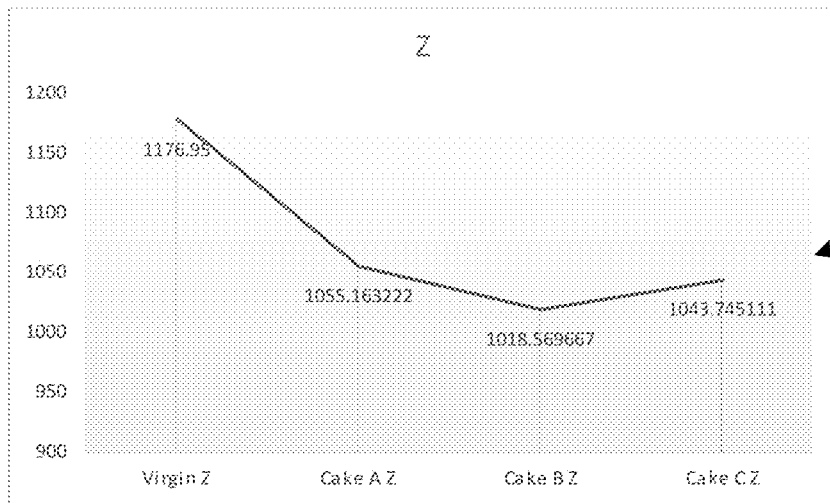
FIG. 10C is a chart showing surface roughness of surface in the z-plane of an anchors in accordance with the present invention.

In reference to FIGS. 10-10C, charts showing the average roughness for difference faces in the SLS build and for different levels of recycle are shown. In FIG. 10A, the roughness level for the down skin or bottom of the xy-surface is shown a test specimen made using SLS from virgin PEKK, first recycle PEKK (Cake A), second recycle PEKK (Cake B), and third recycle PEKK (Cake C). In FIG. 10B, the roughness level for the up skin or top of the xy-surface is shown for test specimen made using SLS from virgin PEKK, first recycle PEKK (Cake A), second recycle PEKK (Cake B), and third recycle PEKK (Cake C). In FIG. 10C, the roughness level for the surface on the out of plane axis is shown for a test specimen made using SLS from virgin PEKK, first recycle PEKK (Cake A), second recycle PEKK (Cake B), and third recycle PEKK (Cake C). The surface in the out-of-plane axis has an average higher roughness resulting from the layer-wise build process.

The inventors have discovered that implants such a suture anchors manufactured from PEKK using SLS and having a roughness of at least 500 Ra (pin) exhibit unexpected levels of favorable osseointegration with adjacent hard tissue through in-vitro and in-vivo studies using animal models. The implants in accordance with the present invention demonstrate bone attachment, sustained capacity for cell proliferation, sufficient attachment, minimal fibrosis, adequate mineral deposition, and efficient use of cell metabolism.

Suture anchors in accordance with the present invention were manufactured in varying sizes from PEKK powder using the SLS process. The suture anchor devices were manufactured with the overall height dimension parallel to the Z build direction (i.e., they were built vertically). The height of all suture anchor devices was 24 mm. Several replicates were manufactured for each size (i.e., 4.5, 5.5, and 6.5 mm sizes) in both virgin and cake material lots. The anchor devices were tested in cadaveric bone (humeral heads) to gauge ease of insertion and the functionality of all instrumentation. In reference to FIG. 11, three printed anchors used in the tests are illustrated. The variation in surface geometry resulting from the SLS process is evident in the picture.

After securing sutures through the tendon and having prepared the footprint, an awl was used to facilitate insertion of the anchor by creating a pilot hole. The sizing of the awl was patient and procedure specific (commonly, the 4.5 mm or 5.5 mm anchors are used for rotator cuff repair and smaller anchors will be used for smaller tendon or ligament to bone repairs). Awl size determination will also be based on the quality of bone and the surgeon's preference for undersizing or oversizing to achieve a secure fit. Once an awl size has been chosen, it is inserted through the arthroscopic portal (usually the lateral portal) and appropriate location for insertion of the suture anchor is chosen. A small mallet is used to tap the end of the awl to create an entry point in the bone for the suture anchor. A positive stop is marked on the awl to indicate the appropriate depth of the anchor (and in turn, the pilot hole).

The suture ends previously threaded through the tendon designated for repair are passed out of the arthroscopic portal and loaded on the anchor by passing the suture ends through the eyelet of the anchor (which is loaded on the inserter). The suture ends can be secured in-hand or locked on the handle of the inserter. The anchor is inserted through the portal down through the portal into the point of entry in a zip-line fashion on the suture. The distal end of the anchor is mated with the inserter. The tip of the anchor is perched at the entry point of the bone tunnel and the tendon is tensioned by pulling on the suture to bring it up to its footprint point. Once appropriate tensioning is achieved, and the tendon is in a satisfactory position. The surgeon sets approximately half of the anchor into the bone tunnel by providing force on the proximal end of the inserter. At this point, the design of the anchor should allow for any fine adjustments to the final positioning of the tendon. Next the rest of the anchor is inserted into the bone, taking into account the length of the suture corresponding to anchor length. Adequate suture laxity must be allowed at the starting point of anchor entry to reach the desired attachment point for the tendon when the anchor is fully secured. The inserted is then retracted from the anchor.

The cadaver evaluation of the SLS printed anchors was supportive. The response from the surgeon and his staff was positive and they found the functionality of the devices and instrumentation suitable to the surgical procedure. The anchor insertion testing evaluated the ability of the anchor to be deployed correctly without damage to the device or the cadaver specimen. The results of this testing demonstrated adequate insertion strength of the anchors and proper functionality of the associated insertion instrumentation. The testing also demonstrated a significant resistance to anchor pullout.

While the present teachings have been described above in terms of specific embodiments, it is to be understood that they are not limited to those disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. An anchor system for securing suture tissue to bone, comprising,
    an anchor having an elongated body comprising a polyaryletherketone (PAEK) polymer selectively sintered in accordance with a CAD file having a geometric description of the anchor, the elongated body extending along a longitudinal axis between a proximal region terminating in a proximal end and a distal region terminating in a distal end configured for insertion into a hole in the bone, an outer surface of the elongated body having a roughness of at least 500 Ra (μ-in),
    a socket at the proximal region of the elongated body, the socket having a socket length extending along the longitudinal axis from an opening at the proximal region, the socket defining a cross-section that has a width in a first dimension D1,
    an inserter extending along an axis and having a protrusion at a distal region thereof, the protrusion having a protrusion length extending along the axis from a base of the protrusion toward a distal tip of the protrusion, the protrusion being configured to matingly engage with the socket, the protrusion defining a cross-section that decreases progressively in width in the dimension D1 along the protrusion length distally from the base of the protrusion toward the distal tip of the protrusion.

2. The system of claim 1, wherein the protrusion cross-section becomes smaller progressively in width in a second dimension D2 along the protrusion length distally from the base of the protrusion toward the distal tip of the protrusion.

3. The system of claim 2, wherein a width of the protrusion in the dimension D1 at the base of the protrusion is less than a width of the opening of the socket in the dimension D1 as specified by the CAD file.

4. The system of claim 3, wherein a width of the protrusion in the dimension D2 at the base of the protrusion is less than a width of the opening of the socket in a dimension as specified by the CAD file.

5. The system of claim 4, wherein D1 is perpendicular to D2, and wherein D1 and D2 are both perpendicular to the longitudinal axis of the elongated body.

6. The system for claim 5, wherein the socket cross-section as specified by the CAD file remains substantially constant in the width in the dimension D1 distally from the opening of the socket along the socket length and the socket cross-section as specified by the CAD file remains substantially constant in a width in the second dimension D2 distally from the opening of the socket along the socket length.

7. The system of claim 1, wherein the width of the protrusion in the dimension D1 at the base of the protrusion is less than the width of the opening of the socket in the dimension D1 as specified by the CAD file by at least a dimensional tolerance factor associated with the selective laser sintering process of the PAEK polymer to form the anchor, and
    wherein the width of the protrusion in the dimension D2 at the base of the protrusion is less than the width of the opening of the socket in the second dimension D2 as specified by the CAD file by at least the dimensional tolerance factor associated with the selective laser sintering process of the PAEK material to form the anchor.

8. The system of claim 7, wherein the cross-section of the opening defines an equilateral quadrilateral.

9. The system of claim 8, further comprising barbs disposed on an outer surface of the body and an eyelet for receiving suture extending transversely through the body.

10. The system of claim 7, wherein the inserter defines a shoulder at the base of the protrusion, and wherein the shoulder abuts a proximal area of the anchor body when the protrusion is matingly engaged with the socket.

11. The system of claim 10, wherein the protrusion is configured so that a distal tip of the protrusion abuts a bottom of the socket when the protrusion is matingly engaged with the socket.

12. The system of claim 1, wherein the width of the protrusion in the dimension D1 at the base of the protrusion is less than the width of the opening of the socket in the dimension D1 as specified by the CAD file by at least 0.25 mm, and
    wherein the width of the protrusion in the dimension D2 at the base of the protrusion is less than the width of the opening of the socket in the dimension D2 as specified by the CAD file by at least 0.25 mm.

13. The system of claim 1, wherein the width of the protrusion in the dimension D1 at the base of the protrusion is less than the width of the opening of the socket in the dimension D1 as specified by the CAD file by at least 0.50 mm, and
    wherein the width of the protrusion in the dimension D2 at the base of the protrusion is less than the width of the opening of the socket in the dimension D2 as specified by the CAD file by at least 0.50 mm.

14. An anchor system for securing suture tissue to bone, comprising,
    an anchor having an elongated body comprising a polyetherketoneketone (PEKK) polymer selectively sintered in accordance with a CAD file having a geometric description of the anchor, the elongated body extending along a longitudinal axis between a proximal region terminating in a proximal end and a distal region terminating in a distal end configured for insertion into a hole in the bone, an outer surface of the elongated body have a roughness of at least 500 Ra (μ-in);
    a socket at the proximal region of the elongated body, the socket having a socket length extending along the longitudinal axis from an opening at the proximal region, the socket defining a cross-section having a width in a first dimension D1;

an inserter extending along an axis and having a protrusion at a distal region thereof, the protrusion having a protrusion length extending along the axis from a base of the protrusion toward a distal tip of the protrusion, the protrusion being configured to matingly engage with the socket, the protrusion defining a cross-section that decreases progressively in width in the dimension D1 along the protrusion length distally from the base of the protrusion toward the distal tip of the protrusion.

15. The system of claim 14, wherein the cross-section of the opening defines an equilateral quadrilateral.

16. The system of claim 15, wherein a width of the protrusion in the dimension D1 at the base of the protrusion is less than a width of the opening of the socket in the dimension D1 as specified by the CAD file.

17. The system of claim 16, wherein the width of the protrusion in the dimension D1 at the base of the protrusion is less than the width of the opening of the socket in the dimension D1 as specified by the CAD file by at least a dimensional tolerance factor associated with the selective laser sintering process of the PEKK polymer.

18. The system of claim 17, wherein the width of the protrusion in the dimension D1 at the base of the protrusion is less than the width of the opening of the socket in the dimension D1 as specified by the CAD file by at least 0.50 mm.

19. The system of claim 17, wherein the socket cross-section remains substantially constant in a width in the dimension D1 distally from the opening of the socket along the socket length.

\* \* \* \* \*